US012806191B2

(12) United States Patent
Kim

(10) Patent No.: US 12,806,191 B2
(45) Date of Patent: Nov. 24, 2026

(54) COMPOUND FOR SUPPRESSING NONSENSE-MEDIATED mRNA DECAY

(71) Applicant: RiboTech Co., Ltd., Seoul (KR)

(72) Inventor: Yoon Ki Kim, Seoul (KR)

(73) Assignee: RiboTech Co., Ltd., Seoul (KR)

( * ) Notice: Subject to any disclaimer, the term of this patent is extended or adjusted under 35 U.S.C. 154(b) by 525 days.

(21) Appl. No.: 18/277,304

(22) PCT Filed: Feb. 15, 2022

(86) PCT No.: PCT/KR2022/002226
§ 371 (c)(1),
(2) Date: Aug. 15, 2023

(87) PCT Pub. No.: WO2022/177267
PCT Pub. Date: Aug. 25, 2022

(65) Prior Publication Data

US 2024/0139183 A1 May 2, 2024

(30) Foreign Application Priority Data

Feb. 16, 2021 (KR) ........................ 10-2021-0020750
Aug. 23, 2021 (KR) ........................ 10-2021-0111192

(51) Int. Cl.
*A61K 31/501* (2006.01)
*A61K 31/4709* (2006.01)
*A61P 21/00* (2006.01)
*A61P 43/00* (2006.01)

(52) U.S. Cl.
CPC ........ *A61K 31/501* (2013.01); *A61K 31/4709* (2013.01); *A61P 21/00* (2018.01); *A61P 43/00* (2018.01)

(58) Field of Classification Search
CPC .............. A61K 31/501; A61K 31/4709; A61K 31/4745; A61K 31/517; A61P 21/00
See application file for complete search history.

(56) References Cited

FOREIGN PATENT DOCUMENTS

| | | | |
|---|---|---|---|
| KR | 10-2009-0074231 | A | 7/2009 |
| KR | 10-1021402 | B1 | 3/2011 |
| KR | 10-2017-0076606 | A | 7/2017 |
| KR | 10-2018-0004400 | A | 1/2018 |
| WO | 2006/122806 | A2 | 11/2006 |
| WO | 2008/044463 | A1 | 4/2008 |
| WO | 2012/052730 | A1 | 4/2012 |
| WO | WO 2012/120048 | * | 9/2012 |
| WO | 2020/060779 | A2 | 3/2020 |
| WO | 2020/076432 | A1 | 4/2020 |

OTHER PUBLICATIONS

Zhe Chen et al., "Exercise protects proliferative muscle satellite cells against exhaustion via the Igfbp7-Akt-mTOR axis", Theranostics, 2020, pp. 6448-6466, vol. 10, No. 14.

Jiajing Cai et al., "The PI3K/mTOR dual inhibitor NVP-BEZ235 stimulates mutant p53 degradation to exert anti-tumor effects on triple-negative breast cancer cells", FEBS Open Bio, 2020, pp. 535-545, vol. 10.

International Search Report for PCT/KR2022/002226 dated, May 26, 2022 (PCT/ISA/210).

Praveen B. Gurpur, et al., "Valproic Acid Activates the PI3K/Akt/mTOR Pathway in Muscle and Ameliorates Pathology in a Mouse Model of Duchenne Muscular Dystrophy", The American Journal of Pathology, Mar. 2009, vol. 174, No. 3, pp. 999-1008 (10 pages).

Xiaohua Chen et al., "Mutant p53 in cancer: from molecular mechanism to therapeutic modulation", Cell Death and Disease, 2022, vol. 13, No. 974, pp. 1-14 (14 pages).

Extended European Search Report dated Jan. 20, 2025 in Application No. 22756465.5.

Communication dated Jun. 29, 2026, in European Application No. 22 756 456.5.

Welch, et al., "PTC124 targets genetic disorders caused by nonsense mutations" , Nature, May 3, 2007, vol. 447, doi: 10.1038/nature05756, pp. 87-91 (7 pages).

Salvatori, et al., "Production of β-globin and adult hemoglobin following G418 treatment of erythroid precursor cells from homozygous (039 thalassemia patients", American Journal of Hematology, 2009, pp. 720-728 (9 pages).

* cited by examiner

*Primary Examiner* — Sahar Javanmard
(74) *Attorney, Agent, or Firm* — Sughrue Mion, PLLC

(57) ABSTRACT

The present invention relates to a compound for inhibition of nonsense-mediated mRNA decay (hereinafter referred to as "NMD") or a pharmaceutically acceptable salt thereof. The present invention aims to prevent or treat NMD-related disease through the NMD-inhibiting compound.

4 Claims, 7 Drawing Sheets

[FIG. 1]
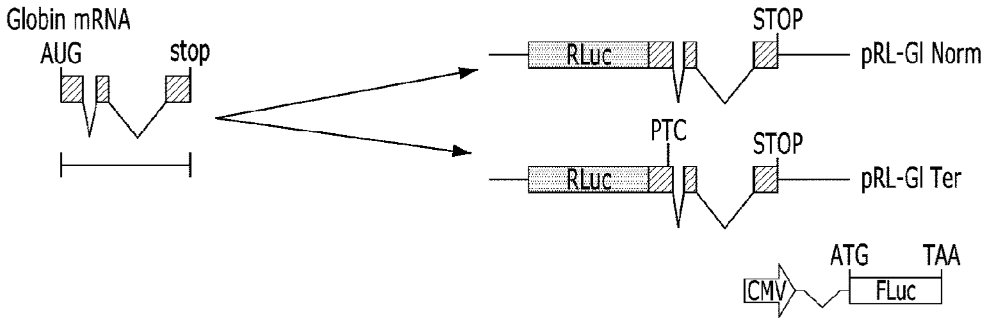
[FIG. 2]
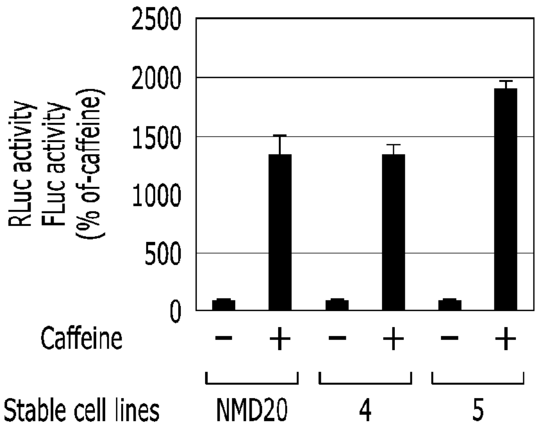
[FIG. 3]
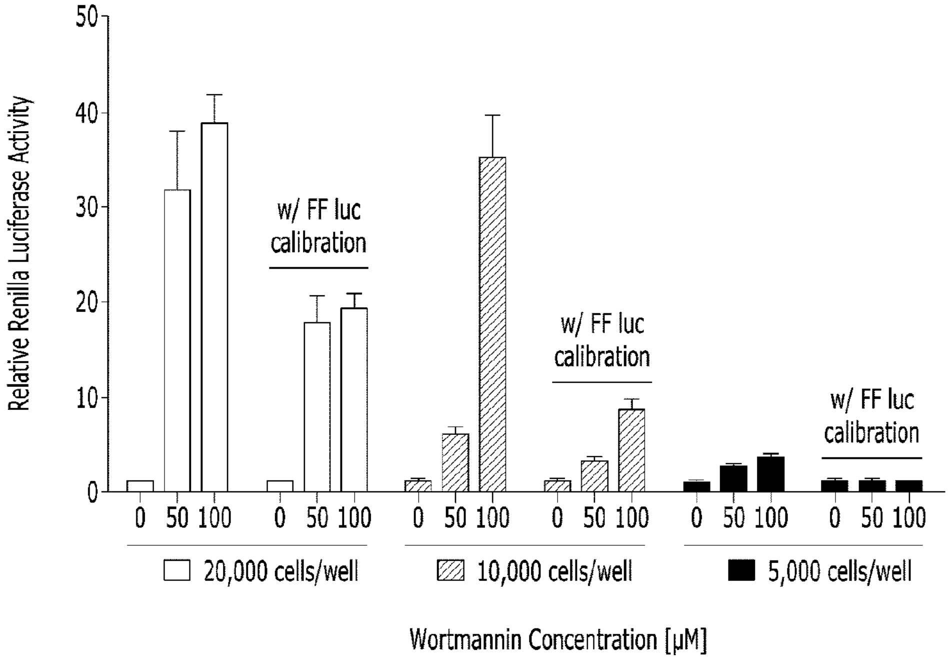

[FIG. 4]
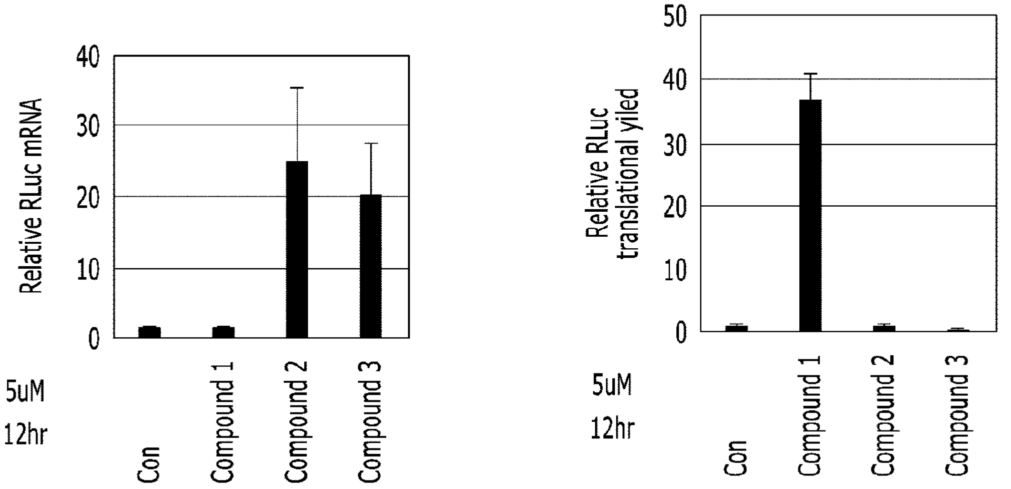
[FIG. 5]
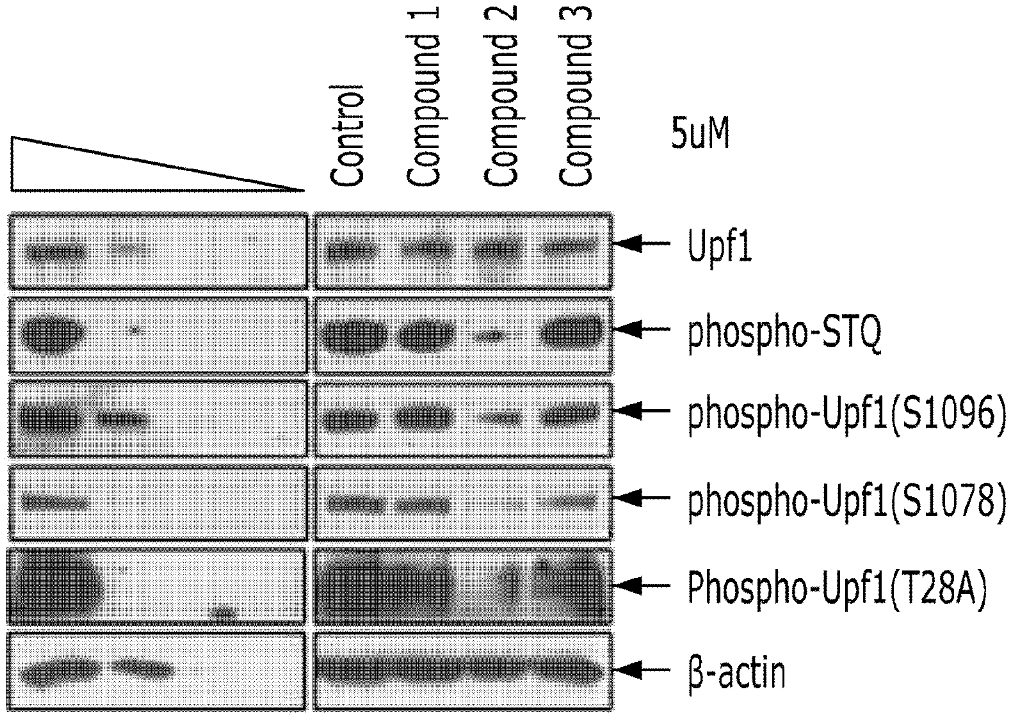

[FIG. 6]
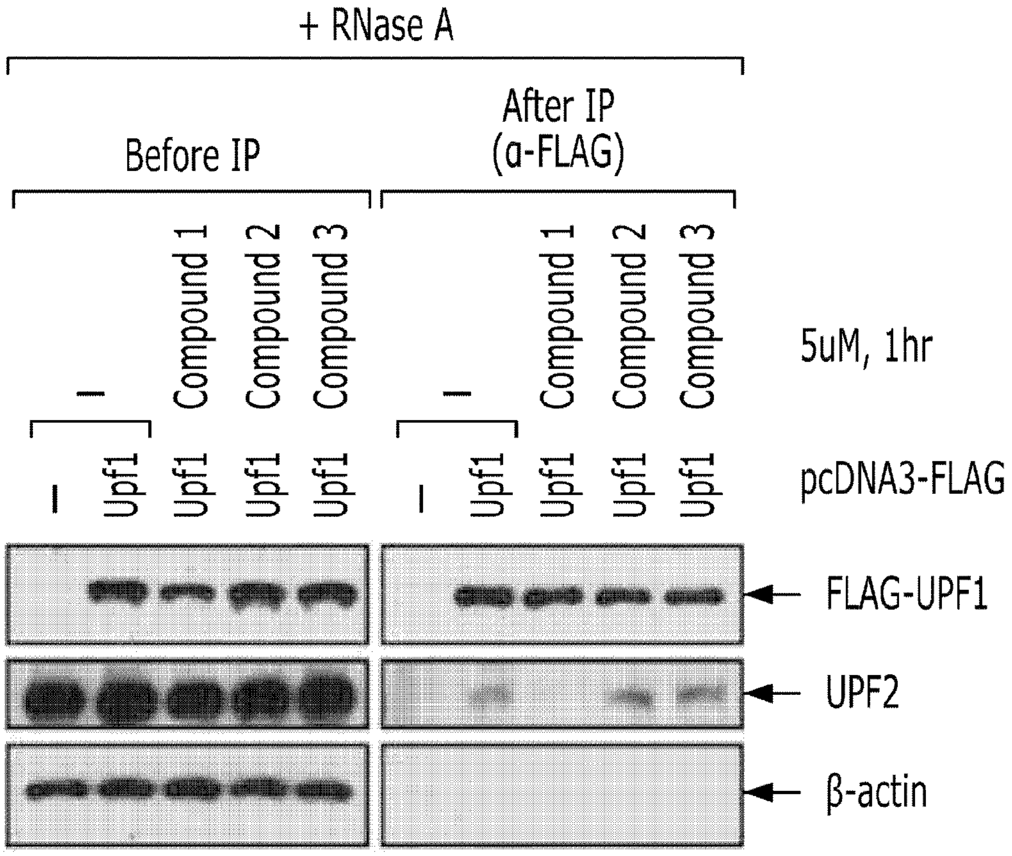

[FIG. 7]
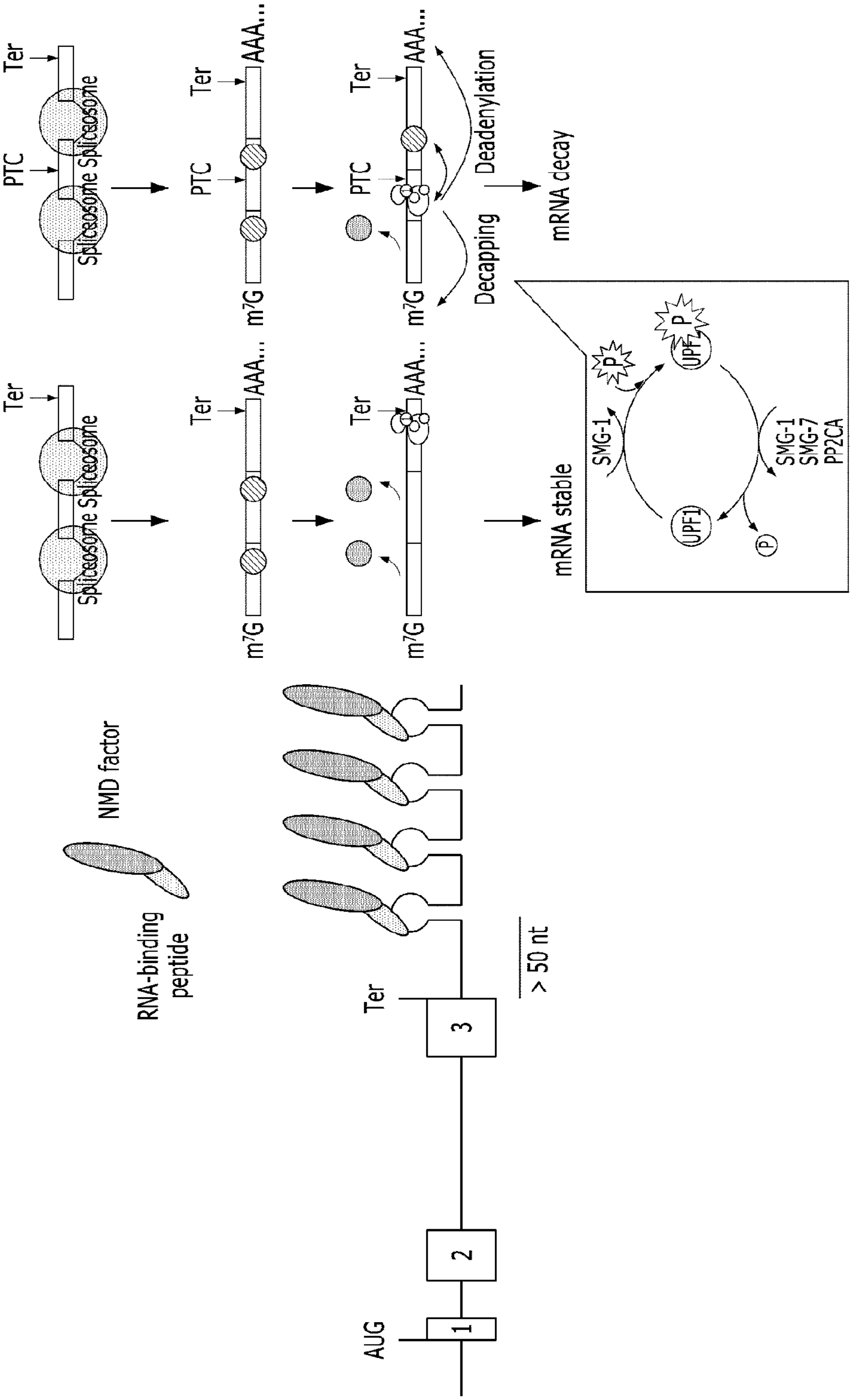

[FIG. 8]
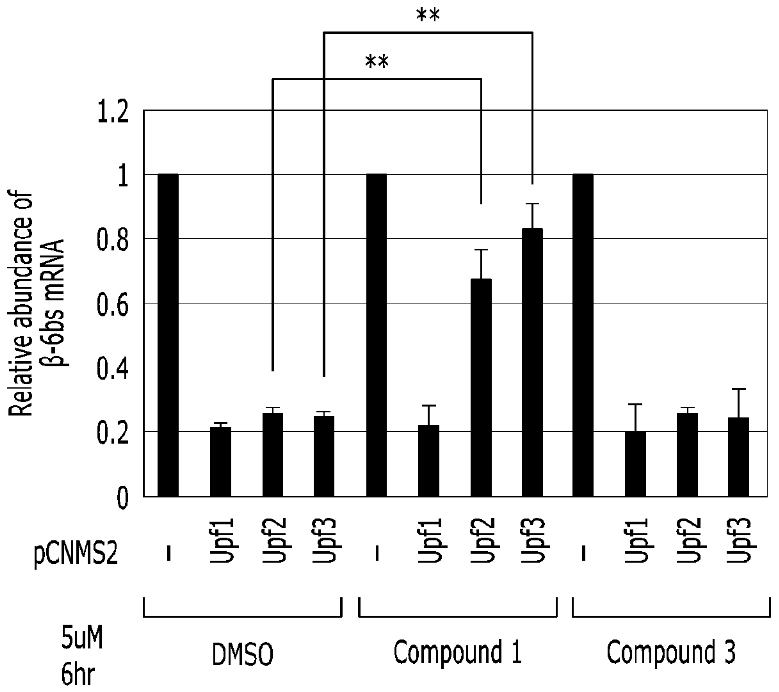
[FIG. 9]
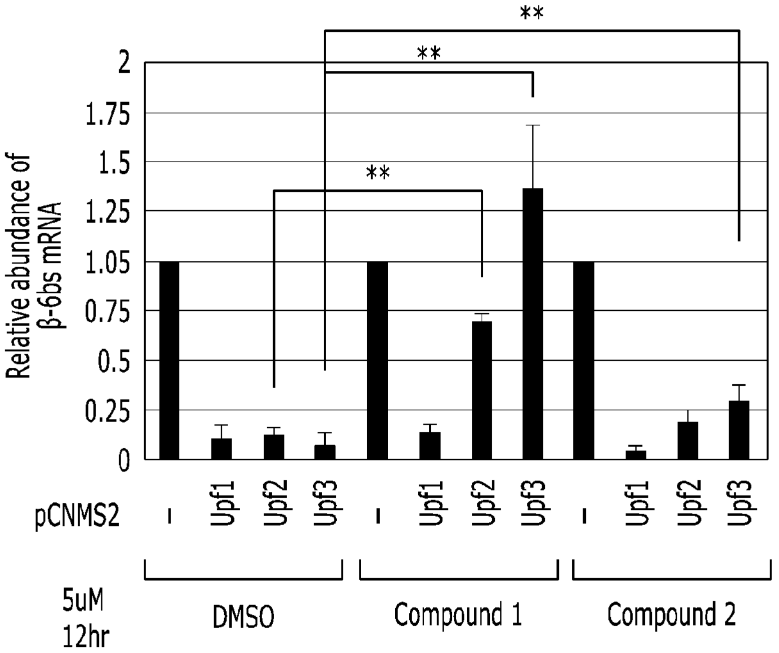

[FIG. 10]
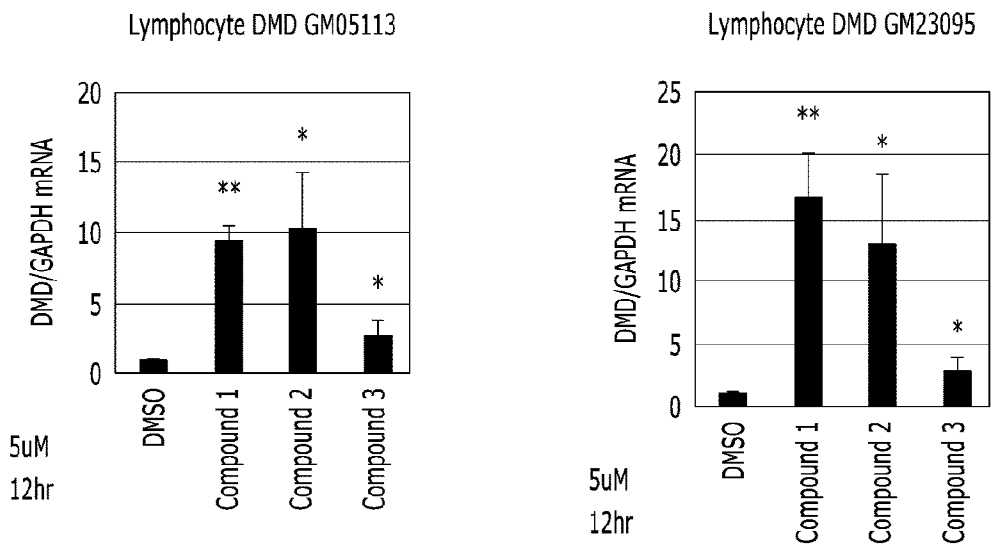

[FIG. 11]
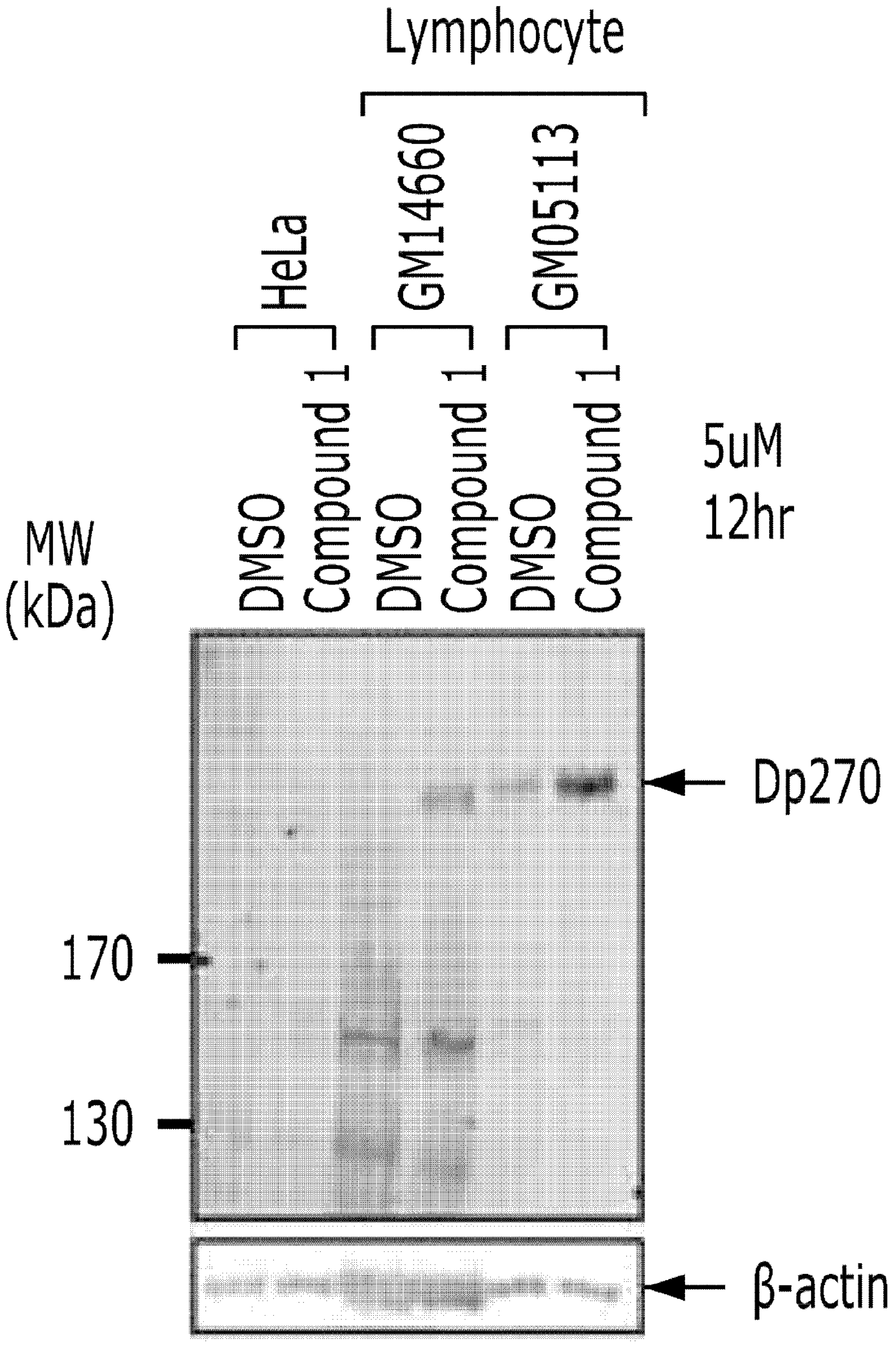

COMPOUND FOR SUPPRESSING NONSENSE-MEDIATED mRNA DECAY

CROSS REFERENCE TO RELATED APPLICATIONS

This application is a National Stage of International Application No. PCT/KR2022/002226 filed Feb. 15, 2022, claiming priority based on Korean Patent Application No. 10-2021-0020750 filed on Feb. 16, 2021, and Korean Patent Application No. 10-2021-0111192 filed on Aug. 23, 2021, the entire disclosures of which are incorporated herein by reference.

TECHNICAL FIELD

The present invention relates to a compound for inhibition of nonsense-mediated mRNA decay (hereinafter referred to as "NMD") and a pharmaceutically acceptable salt thereof. The present invention aims to prevent or treat NMD-related disease through the NMD-inhibiting compound.

BACKGROUND ART

All human genes perform final unique functions by expressing an appropriate amount at appropriate time and location. If a problem occurs in a process of regulating the appropriate expression of a gene, the abnormally expressed gene interferes with normal cell functions, resulting in numerous cancers and hereditary diseases.

It is known that about 30% of genetic diseases known so far are caused by aberrant mRNAs produced by an abnormal process, that is, nonsense mutation. The main causes of nonsense mutagenesis are not only mutations generated on DNA sequences such as mistakes in DNA recombination and replication, but also abnormal or inefficient intracellular mechanisms such as aberrant transcription, inefficient splicing, and frameshift mutations.

mRNAs with nonsense mutations express proteins shorter than normal lengths, which may inhibit normal cell functions. Fortunately, however, most aberrant mRNAs are recognized by the NMD mechanism, which is a quality inspection mechanism present in cells, and are eliminated from cells at a much faster rate than normal mRNAs. That is, cells may selectively recognize/remove aberrant mRNA that may harm the cells themselves by using the NMD mechanism.

If mRNAs aberrantly produced for various reasons are not eliminated by NMD, short proteins that may inhibit cell functions are produced, resulting in cellular carcinogenesis and various genetic diseases. On the contrary, even slight aberrant mRNAs are quickly eliminated by NMD to inhibit the normal function of cells, which are also directly related to the development of various genetic diseases (Korean Patent Registration No. 10-1021402).

Currently, many therapies have been developed for the treatment of NMD-related diseases. For example, drug development such as PTC 124 (generic name: ataluren), which is a 1,2,4-oxidiazole compound, is in progress for mutation-specific treatment of genetic diseases, such as Duchenne muscular dystrophy (hereinafter, DMD).

DISCLOSURE

Technical Problem

Development of an effective therapeutic agent for effectively treating NMD-related genetic disease by inhibiting NMD is still required.

Technical Solution

One object of the present invention provides a pharmaceutical composition capable of being used for the prevention or treatment of NMD-related genetic disease, including a compound as an active ingredient, by providing the compound for effectively inhibiting NMD (hereinafter, also referred to as "NMD-inhibiting compound").

Another object of the present invention provides a use of the NMD-inhibiting compound for the prevention or treatment of NMD-related genetic disease.

Still another object of the present invention provides a method of preventing or treating NMD-related genetic disease in a subject in need of treatment by administering an effective amount of an NMD-inhibiting compound to the subject.

Advantageous Effects

Since the NMD-inhibiting compound of the present invention lowers the NMD efficiency, the NMD-inhibiting compound may be effectively used for preventing or treating various diseases, particularly genetic diseases caused by NMD due to PTC.

DESCRIPTION OF DRAWINGS

FIG. 1 is a schematic diagram illustrating cell lines for constitutive expression of NMD target mRNA for high-throughput screening (HTS) of an NMD inhibitor.

FIG. 2 illustrates results of treating the cell lines of FIG. 1 with caffeine, which is a non-specific NMD inhibitor.

FIG. 3 illustrates results of treating the cell lines of FIG. 1 with Wortmannin, which is a non-specific NMD inhibitor.

FIG. 4 illustrates results of confirming the expression efficiency of renilla luciferase (RLuc) at mRNA and protein levels after the cell lines of FIG. 1 are treated with Compounds 1 to 3.

FIG. 5 illustrates results of analyzing an effect of treatment with Compounds 1 to 3 on phosphorylation of upstream frameshift 1 (UPF1).

FIG. 6 illustrates results of analyzing an effect of treatment with Compounds 1 to 3 on binding between UPF1 and UPF2.

FIG. 7 is a schematic diagram of a method for artificially reducing the amount of reporter mRNA by artificially tethering proteins Upf1, Upf2, and Upf3X acting in each step of NMD to 3' UTR of reporter mRNA. Through this method, it is possible to determine a precise step in which a specific compound affects NMD.

FIG. 8 illustrates a result of confirming a level of β-6bs mRNA, which is reporter mRNA, after the cell lines are treated with Compound 1 or 3, respectively, using the method of FIG. 7.

FIG. 9 illustrates a result of confirming a level of β-6bs mRNA, which is reporter mRNA, after the cell lines are treated with Compound 1 or 2, respectively, using the method of FIG. 7.

FIG. 10 illustrates a result of confirming the mRNA level of a dystrophin gene, which is an NMD target gene, after treating cells derived from patients with DMD with Compounds 1 to 3, respectively.

FIG. 11 illustrates a result of confirming the level of a dystrophin protein after treating cells derived from patients with DMD with Compound 1.

BEST MODE FOR THE INVENTION

The present invention provides a pharmaceutical composition for preventing or treating nonsense-mediated mRNA decay (NMD)-related disease, including a compound represented by any one of the following Chemical Formulas 1 to 3 or a pharmaceutically acceptable salt thereof as an active ingredient; a use of the compound or a pharmaceutically acceptable salt thereof for the prevention or treatment of NMD-related disease; or a method for preventing or treating NMD-related disease, including administering the compound or a pharmaceutically acceptable salt thereof to a subject in need thereof.

[Chemical Formula 1]

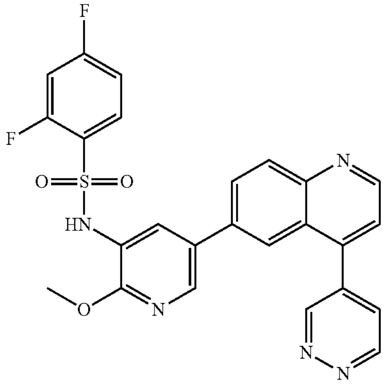

[Chemical Formula 2]

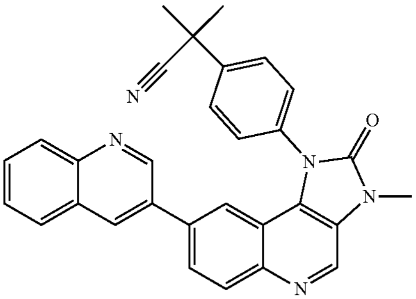

[Chemical Formula 3]

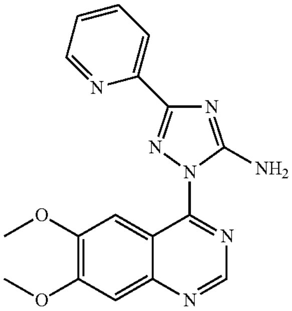

The NMD-related disease may be related to mutation genes including a nonsense mutation, or may be genetic disease caused by NMD due to a premature termination codon (PTC) associated with a nonsense mutation or frameshift mutation.

The NMD-related genetic disease may be cystic fibrosis, muscular dystrophy (e.g., Duchenne muscular dystrophy, Becker muscular dystrophy, Ullrich's disease, congenital muscular atrophy dystrophy, or Limb-girdle muscular dystrophy, etc.), autosomal dominant polycystic kidney disease (ADOKD), ataxia telangiectasia, beta-thalassemia, factor VII deficiency, familial atrial fibrillation, hemophilia B, hepatic carnitine palmitoyltransferase 1A deficiency (CPT1A), heritable pulmonary arterial hypertension (HPAH), late infantile neuronal ceroid lipofuscinosis (LNCL), leukocyte adhesion deficiency 1 (LAD1), methylmalonic acidemia (MMA), Hurler syndrome, nephropathic cystinosis, obesity, peroxisome biogenesis disorder (PBD), renal tubular acidosis (RTA), retinitis pigmentosa (RP), Rett syndrome (RTT), spinal muscular atrophy (SMA), Stuve-Wiedemann syndrome (SMS), X-linked nephrogenic diabetes insipidus (XNDI) or Usher syndrome (USH1).

Additionally, in addition to the above-mentioned NMD-related genetic disease, the NMD-related disease of the present invention may be various cancers (e.g., hereditary diffuse gastric cancer (HDGC), P53 gene mutation-related cancer, or APC gene mutation-related cancer) caused by the presence of premature termination codons.

The present invention provides a compound for inhibition of NMD or a pharmaceutically acceptable salt thereof.

In one embodiment, the compound for inhibition of the NMD of the present invention is represented by the following Chemical Formula 1. In the present invention, the compound of the following Chemical Formula 1 is also simply referred to as "Compound 1".

[Chemical Formula 1]

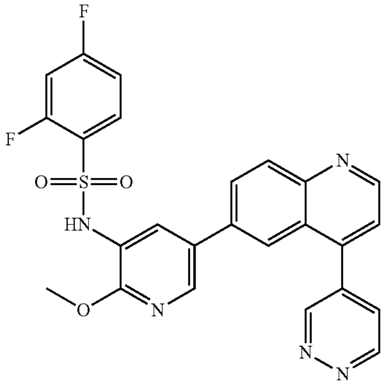

The compound of Chemical Formula 1 is referred to as a code number of GSK2126458 or a generic name of Omipalisib, and a compound name thereof is 2,4-Difluoro-N-{2-(methyloxy)-5-[4-(4-pyridazinyl)-6-quinolinyl]-3-pyridinyl}benzenesulfonamide. It is known that the compound of Chemical Formula 1 exhibits an anticancer effect by binding to PI3K in a PI3K/mTOR signaling pathway to suppress PI3K (https://pubchem.ncbi.nlm.nih. gov/compound/Omipalisib). Preparation of Compound 1 and its use are disclosed in WO 2008/144463, particularly Example 345, etc.

In another embodiment, the compound for inhibition of the NMD of the present invention is represented by the following Chemical Formula 2. In the present invention, the compound of the following Chemical Formula 2 is also simply referred to as "Compound 2".

[Chemical Formula 2]

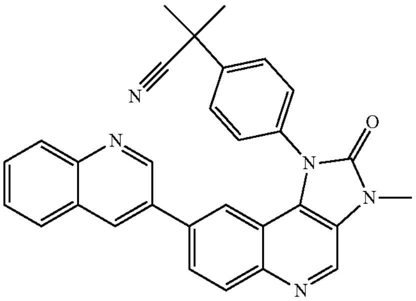

The compound of Chemical Formula 2 is referred to as a code number of BEZ235 or a generic name of Dactolisib, and a compound name thereof is 2-methyl-2-{4-[3-methyl-2-oxo-8-(quinolin-3-yl)-2,3-dihydro-1H-imidazo[4,5-c]quinolin-1-yl]phenyl}propanenitrile.

It is known that the compound of Chemical Formula 2 binds to PI3K kinase and mTOR kinase in the PI3K/AKT/mTOR signaling pathway to exhibit the activities of killing tumor cells and inhibiting the growth of PI3K/mTOR-overexpressing tumor cells (https://pubchem.ncbi.nlm.nih.gov/compound/11977753). Preparation of Compound 2 and its use are disclosed in WO 2006/122806, particularly Example 7, etc.

In still another embodiment, the compound for inhibition of the NMD of the present invention is represented by the following Chemical Formula 3. In the present invention, the compound of the following Chemical Formula 3 is also simply referred to as "Compound 3".

[Chemical Formula 3]

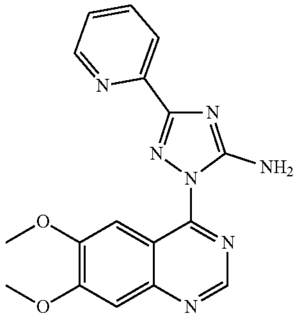

The compound of Chemical Formula 3 is referred to as a code number of CP-466722, and a compound name thereof is 1-(6,7-Dimethoxy-4-quinazolinyl)-3-(2-pyridinyl)-1H-1,2,4-Triazol-5-amine.

In the present invention, each of the compounds represented by Chemical Formulas 1 to 3 is collectively referred to as "the compound of the present invention."

The compounds of the present invention may exist in the form of pharmaceutically acceptable salts.

The "pharmaceutically acceptable salt" or "salt" is used herein to refer to acid or base addition salts suitable or compatible for the treatment of patients. Examples of inorganic acids which form suitable salts may include not only hydrochloric, hydrobromic, sulfuric and phosphoric acids, but also metal salts, such as sodium monohydrogen orthophosphate and potassium hydrogen sulfate. Examples of organic acids which form suitable salts may include not only mono-, di- and tricarboxylic acids, such as glycolic acid, lactic acid, pyruvic acid, malonic acid, succinic acid, glutaric acid, fumaric acid, malic acid, tartaric acid, citric acid, ascorbic acid, maleic acids, benzoic acid, phenylacetic acid, cinnamic acid and salicylic acid, but also sulfonic acids such as p-toluenesulfonic acid and methanesulfonic acid. Mono- or di-acid salts may be formed, and these salts may exist in hydrated, solvated or substantially anhydrous form. In general, acid addition salts of the compounds of the present invention are more soluble in water and various hydrophilic organic solvents and generally exhibit higher melting points compared to free base forms thereof. The selection of suitable salts is known to those skilled in the art. Other non-pharmaceutically acceptable salts, such as oxalate, may be used in the isolation of the compounds of the present invention, for example, for laboratory use or subsequent conversion to pharmaceutically acceptable acid addition salts. Examples of inorganic bases that form suitable salts may include lithium, sodium, potassium, calcium, magnesium, or barium hydroxides. Examples of organic bases that form suitable salts may include aliphatic, cycloaliphatic or aromatic organic amines, such as methylamine, trimethylamine and picoline or ammonia. Accordingly, in some examples, salts of the present invention to be considered may include alkyl, dialkyl, trialkyl or tetra-alkyl ammonium salts. In a specific embodiment, salts of the present invention to be considered may include L-arginine, benentamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts, but are not limited thereto.

The selection of suitable salts is known to those skilled in the art. For example, the compound of Chemical Formula 2 may exist in the form of tosylate.

In addition, the compounds of the present invention also include, without limitation, all possible optical isomers as well as pharmaceutically acceptable salts thereof. Stereoisomers of the compounds of the present invention may be prepared using methods known in the art.

Additionally, the compounds of the present invention may be prepared in crystalline or amorphous forms. If the compounds are prepared in crystalline forms, the compounds may optionally be hydrated or solvated.

The compounds of the present invention may be formulated as any therapeutic pharmaceutical composition or in a form suitable for use in any method disclosed herein, such as preventive or therapeutic methods.

Unless otherwise stated herein, the compounds of the present invention as active ingredients of therapeutic agents include any pharmaceutically acceptable salts thereof, and all of these pharmaceutically acceptable salts are to be considered within the scope of the present invention. For convenience of description, the compound may be simply abbreviated as a compound of Chemical Formula above or a compound of the present invention.

The compound of the present invention or pharmaceutically acceptable salts thereof may inhibit nonsense-mediated mRNA decay (NMD). Accordingly, Compounds 1 to 3 of the present invention exhibit an effect of preventing or treating NMD-related disease.

In one embodiment, the present invention relates to a pharmaceutical composition for preventing or treating NMD-related disease, including the compound of the present invention or a pharmaceutically acceptable salt thereof as an active ingredient. The compound or the pharmaceutically acceptable salt thereof may be included in an effective amount.

In another embodiment, the present invention relates to a use of a compound of the present invention, or a pharmaceutically acceptable salt thereof, for the prevention or treatment of NMD-related disease.

In still another embodiment, the present invention relates to a method for preventing or treating NMD-related disease, including administering a compound of the present invention or a pharmaceutically acceptable salt thereof to a subject in need thereof. The compound or the pharmaceutically acceptable salt thereof may be administered in a therapeutically effective amount.

As used herein, the term "effective amount" or "therapeutically effective amount" is used interchangeably herein, and refers to an amount of a compound, formulation, substance or composition effective to achieve a particular biological result, as described herein. As used herein, the term "therapeutically effective amount" refers to an amount of the compound of the present invention of biological or medical response of a subject, such as alleviating symptoms, alleviating conditions, slowing or delaying the progression of a disease, preventing a disease, and the like.

As used herein, the term "subject" or "patient" includes human and non-human animals. Non-human animals include vertebrates, such as mammals and non-mammals, such as non-human primates, sheep, cats, horses, cows, chickens, dogs, mice, rats, goats, rabbits, and pigs. Preferably, the subject is a human. Except for the aforementioned case, the term "patient" or "subject" is used interchangeably herein.

As used herein, the term "treat", "treating" or "treatment" of any disease, condition or disorder means alleviating or ameliorating the disease, condition or disorder (i.e., delaying or preventing the occurrence of a condition or at least one of clinical symptoms thereof); or alleviating or ameliorating at least one somatic parameter or biomarker associated with the disease, condition or disorder, including one that is not perceptible to a patient.

As used herein, the term "prevent", "preventing" or "prevention" of any disease, condition or disorder means preventive treatment of the disease, condition or disorder; or delaying the onset or progression of the condition or disorder.

In a specific embodiment, the NMD-related disease may be a disease which is responsive to NMD inhibition.

In another specific embodiment, the NMD-related disease may be related to mutation genes including a nonsense mutation, and may be, for example, genetic disease caused by the nonsense mutation.

In still another specific embodiment, the NMD-related disease may be genetic disease caused by NMD due to a premature termination codon (PTC) associated with a nonsense mutation or frameshift mutation. Accordingly, the NMD-related disease of the present invention may be selected based on nucleotide sequences of genes having PTC.

As used herein, the term "nonsense-mediated RNA decay (NMD)" refers to a mechanism that mediates the decay of mRNA including a premature translational termination codon. Specifically, the NMD is a cell mechanism that specifically recognizes and decays a transcript including a premature termination codon (PTC) that has been introduced into mRNA by mutation, translational error, and aberrant splicing. Upon translation, the corresponding mRNA produces a short form of encoded protein. An NMD surveillance mechanism reduces or prevents the formation of these defective proteins and peptides. It is known that about ⅓ of all genetic diseases and some forms of cancers are caused by nonsense or frameshift mutation introducing PTC, and the NMD may regulate clinical phenotypes of these diseases. Accordingly, the regulation of NMD (i.e., inhibition or increase of NMD) may provide a potential therapeutic benefit.

As used herein, the term "premature translation termination" refers to a result of a mutation that changes the codon corresponding to an amino acid to a stop codon, and the term "premature termination codon (PTC)" or "premature stop codon" refers to a change in a codon corresponding to an amino acid to a stop codon.

As used herein, the term "nonsense mutation" is a point mutation that changes a codon corresponding to an amino acid to a stop codon.

As used herein, the term "frameshift mutation" refers to a genetic mutation caused by deletion or insertion of a DNA sequence that shifts in a direction in which the sequence is read.

As used herein, the term "inhibition of NMD" refers to a decrease in the activity of NMD and a decrease in the decay of defective mRNA in cells by any measurable amount, compared to cells without NMD inhibition. The NMD inhibition may be achieved by various methods, such as blocking the function of a protein component of an NMD pathway, inhibiting translation, or allowing a translational machine to bypass a premature stop codon ("translational bypass therapy (TBT)" or "read-through") (e.g., see the literature [Bashyam, Recent Patents on DNA & Gene Sequences 2009, 3, 7-15]).

In one embodiment, the compound of the present invention may act on any protein of proteins UPF1, UPF2, UPF3X, eIF4AIII, PNRC2, etc. acting on each step of NMD or any step involved in any protein. For example, the compound of the present invention may inhibit the efficiency of NMD by targeting UPF1, which is an important factor for NMD.

In a specific embodiment, the compound of the present invention, particularly Compound 1, exhibits an NMD inhibitory effect by inhibiting the binding of UPF1 and UPF2, which are major proteins of NMD.

In another embodiment, the compound of the present invention, particularly Compound 2, exhibit an NMD inhibitory effect by inhibiting UPF1 phosphorylation, which is a key step in NMD.

In still another embodiment, Compound 3 exhibits an NMD inhibitory effect by targeting a pre-UPF1 step.

As used herein, the term "NMD-related disease" refers to a disease that is responsive to NMD inhibition, and a disease in which a disease phenotype is reduced by NMD inhibition. A patient with such a disease phenotype may be diagnosed, for example, by determining whether or not to have a mutation, such as a nonsense mutation or frameshift mutation that produces PTC, by a conventional method. Alternatively, the patient may be screened by measuring a PTC bearing gene level.

Accordingly, the patient or subject to which the compound of the present invention or the pharmaceutically acceptable salt thereof is applied may be a patient or subject having a nonsense mutation that produces PTC. In another example, the NMD-related disease of the present invention may be a disease caused by NMD due to mutations such as a nonsense mutation or frameshift mutation that produces PTC. Examples of several genetic diseases caused by the nonsense mutation are shown in Table 1.

TABLE 1

| Gene name | Phenotype |
|---|---|
| HBB(β-Globin) | 5' PTC: recessively inherited β-thalassaemia major; heterozygotes healthy<br>3' PTC: dominantly inherited β-thalassaemia intermedia |
| RHO (Rhodopsin) | 5' PTC: recessively inherited blindness; heterozygotes have abnormalities on retinogram, but no clinical disease<br>3' PTC: dominantly inherited blindness |
| SOX 10 (SRY-box 10) | 5' PTC: haploinsufficiency leading to congenital neurosensory deafness and colonic agangliosis<br>3' PTC: dominantly inherited neural developmental defect including neurosensory deafness, colonic agangliosis, peripheral neuropathy and central dysmyelinating leukodystrophy |
| IFNGR1 (Interferon-γ receptor) | 5' PTC: recessively inherited susceptibility to mycobacterial infection; heterozygotes normal<br>3' PTC: dominantly inherited susceptibility to mycobacterial infection |
| CRX (Cone-rod homeobox containing gene) | 5' PTC: no homozygotes to date; heterozygotes normal<br>3' PTC: dominantly inherited Leber congenital amaurosis |
| ROR2 (Receptor tyrosine kinase-like orphan receptor 2) | 5' PTC: recessively inherited Robinow syndrome (orodental abnormalities, hypoplastic genitalia, multiple rib/vertebral anomalies); heterozygotes normal<br>3' PTC: dominantly inherited brachydactyly type B (shortening of digits and metacarpals) |
| CLCN1 (Chloride channel 1, skeletal muscle) | 5' PTC: recessively inherited Becker disease<br>3' PTC: dominantly inherited Thomsen disease (muscular disorder characterized by muscle stiffness and an inability of the muscle to relax) |
| VWF (von willebrand factor) | 5' PTC: recessively inherited type 3 von willebrand disease; heterozygotes normal<br>3' PTC: dominantly inherited type 2A 3 von willebrand disease |
| F10 (Coagulation factor X) | 5' PTC: recessively inherited bleeding tendency; heterozygotes normal<br>3' PTC: dominantly inherited bleeding tendency |
| MPN (Myelin protein zero) | 5' PTC: haploinsufficiency, Charcot-Marie-Tooth disease (neuropathy with loss of muscle tissue and touch sensation)<br>3' PTC: dominant negative or gain-of-function, congenital hypomyelinating neuropathy |
| ELN (Elastin) | 5' PTC: haploinsufficiency, supravalvular aortic stenosis, valvular heart disease<br>3' PTC: dominant negative or gain-of-function, congenital hypomyelinating neuropathy |
| COL1A1 (Collagen type I, α1) | 5' PTC: dominantly inherited, osteogenesis imperfecta (OI) type I (mild form)<br>3' PTC: OI type II-IV (severe form) |
| ATM (Ataxia-telangiectasia mutated gene) | 5' PTC: mild form of ataxia<br>3' PTC: severe form with short survival time |
| SMN1 (Survival motor neuron gene) | 5' PTC: spinal muscular atrophy (SMA) type III (mild form)<br>3' PTC: SMA type I (severe form) |
| DMD (Dystrophin) | PTCs at different positions can cause mild to severe phenotype, however, most commonly 5' PTCs cause severe forms of muscular dystrophy (DMD)<br>3' PTCs cause mild forms of muscular dystrophy (BMD) |
| CFTR (Cystic fibrosis transmembrane conductance regulator gene) | PTCs at different positions can cause mild to severe phenotype, however, most commonly 5' PTC: severe form of cystic fibrosis<br>3' PTC: mild form of cystic fibrosis. Patients with less efficient NMD respond better to nonsense suppression treatment. |
| PAX6 (Paired box gene 6) | 5' PTC: aniridia, congenital absence of the iris<br>3' PTC: not detected, however, dominant negative protein is predicted to show severe phenotype |
| EDAR (Ectodysplasin-A receptor gene) | 5' PTC: autosomal recessive HED (hypohidrotic ectodermal dysplasia)<br>3' PTC: autosomal dominant HED |

TABLE 1-continued

| Gene name | Phenotype |
|---|---|
| SCNN1B (Beta subunit of sodium channel) | 5' PTC: autosomal recessive PHA1 (pseudohypoaldosteronism I)<br>3' PTC: dominant Liddle syndrome |

In a more specific embodiment, the NMD-related genetic disease caused by the presence of the PTC may be cystic fibrosis, muscular dystrophy, autosomal dominant polycystic kidney disease (ADOKD), ataxia telangiectasia, beta-thalassemia, factor VII deficiency, familial atrial fibrillation, hemophilia B, hepatic carnitine palmitoyltransferase 1A deficiency (CPT1A), heritable pulmonary arterial hypertension (HPAH), late infantile neuronal ceroid lipofuscinosis (LNCL), leukocyte adhesion deficiency 1 (LAD1), methylmalonic acidemia (MMA), Hurler syndrome, nephropathic cystinosis, obesity, peroxisome biogenesis disorder (PBD), renal tubular acidosis (RTA), retinitis pigmentosa (RP), Rett syndrome (RTT), spinal muscular atrophy (SMA), Stuve-Wiedemann syndrome (SMS), X-linked nephrogenic diabetes insipidus (XNDI) or Usher syndrome (USH1), but is not limited thereto. For example, any disease known in the art to have a PTC-generating mutation gene is included within the scope of the NMD-related disease of the present invention. Alternatively, all diseases known in the art to have an effect of ameliorating or treating a disease through an NMD inhibition mechanism are also included in the scope of the NMD-related disease of the present invention.

In a specific embodiment, the NMD-related disease that may be prevented or treated by the compounds of the present invention may be muscular dystrophy, specifically, Duchenne muscular dystrophy, Becker muscular dystrophy, Ullrich's disease, congenital muscular atrophy dystrophy, or Limb-girdle muscular dystrophy.

In another specific embodiment, the NMD-related disease caused by the presence of the PTC may be cancer, particularly, hereditary diffuse gastric cancer (HDGC), cancer associated with P53 gene mutations (e.g., Li-Fraumeni syndrome, human breast cancer) or cancer associated with APC gene mutations (e.g., colon cancer and familial adenomatous polyposis).

Duchenne muscular dystrophy (DMD) is a rare and intractable muscle disease caused by the generation of PTC in a dystrophin gene and rapid elimination of the PTC by NMD. 98% or more of DMD mutations cause premature termination of a dystrophin open reading frame at various points over an 11 kb length.

Beta-thalassemia is a blood disorder that reduces hemoglobin production. In β°39-thalassemia, stop codon mutations result in premature translational termination and cause destabilization of mRNA through nonsense-mediated decay. From studies in the literature [Salvatori et al., Am. J. Hematol., 84 (11): 720-8 (2009)], etc., it has been suggested that beta-thalassemia may be prevented or treated through NMD inhibition.

It is known or suggested in the art that all of the above-mentioned diseases may be prevented or treated through NMD inhibition. For example, the literature for cystic fibrosis [Welch et al., Nature 447, 87-91 (2007)], the literature for Ulrich's disease [Usuki et al., Molecular Therapy 14: 351-360 2006], and the literature for HDGC [Karam et al., Oncogene 27:4255-4260 (2008)], and the like may be seen. Other NMD-related genetic diseases and cancers have already been reported in many literatures (for example, see literatures [Miller & Pearce, Mutat Res Rev Mutat Res.

762:52-64 (2014)], [Holbrook et al., Nature Genetics 36:801-808 (2004)], [Supek et al., Trends Genet. 37:657-668 (2021)], [Khajavi et al., Eur J Hum Genet. 14:1074-1081 (2006)], etc.).

As used herein, the term “composition” or “pharmaceutical composition” refers to a mixture of the compound of the present invention with one or more pharmaceutically acceptable carriers. The pharmaceutical composition facilitates administration of the compound to a patient or subject.

Accordingly, the present invention provides a pharmaceutical composition including a compound of the present invention or a pharmaceutically acceptable salt thereof as an active ingredient and further including a pharmaceutically acceptable carrier. The pharmaceutically acceptable carrier is a non-active ingredient, that is, a pharmaceutically acceptable excipient, and may be appropriately selected by those skilled in the art by referring to the literature [Handbook of Pharmaceutical Excipients] and the like.

Suitable routes of administration include, but are not limited to, oral administration, and parenteral administration, such as intramuscular, intravenous, or subcutaneous administration.

MODES OF THE INVENTION

The present invention will be described in more detail through Examples. These Examples are to explain the present invention in more detail, and it will be apparent to those skilled in the art that the scope of the present invention is not limited by these Examples in accordance with the gist of the present invention.

Example 1. Construction of Cell Lines for NMD Inhibitor Detection

In order to measure NMD efficiency, mRNA was generally extracted from cells and the amount of mRNA was confirmed through RT-PCR, but such a method had limitations in performing high-throughput screening (HTS), so that it is necessary to develop a method capable of being easily quantified.

Accordingly, the present invention provided an efficient NMD inhibitor search method as illustrated in FIG. 1. Beta-thalassemia was an NMD-related genetic disease and was known to be related to a beta-globin gene. That is, in the beta-globin gene of a person with beta-thalassemia, compared to a normal person, a premature termination codon (PTC) gene is expressed.

In Example 1, a beta-globin normal gene or the gene including a premature termination codon (PTC) found in genetic diseases was inserted into the downstream of a chemiluminescence gene, Renilla luciferase (RLuc). Normal gene-inserted mRNA was not targeted by NMD, whereas when a gene having PTC was inserted, the mRNA became a NMD target, and as a result, mRNA was quickly broken down and the expression level of RLuc was reduced.

Accordingly, a HeLa cell line constitutively expressing the NMD-target mRNA was prepared, and simultaneously, the cell line was designed to constitutively express a firefly luciferase (FLuc) gene, which was not a target of NMD, and a total of three cell lines NMD20, NMD4, and NMD5 with the same composition were obtained. In order to confirm whether the HeLa cell line prepared above was suitable for measuring NMD efficiency, the following two experiments were performed.

First, each of the prepared cell lines was treated with caffeine, which was known as a non-specific NMD inhibitor, to confirm the degree of RLuc activity to FLuc activity. After treatment with a reagent for 12 hours, a total protein was isolated from the cells. Then, the expression levels of RLuc and FLuc proteins were measured by dual luciferase assay. As a result, as illustrated in FIG. 2, it was confirmed that the expression level of RLuc increased to about 1,300-fold to about 2,000-fold in the caffeine-treated group, as compared to a caffeine-untreated group. These results indicated that the cell lines well reflected the efficiency of NMD.

Additionally, it was attempted to determine whether the prepared HeLa cell line was suitable for performing high-throughput screening (HTS). Experiments were performed by optimizing the conditions such as the number of cells, the amounts of used reagent and buffer, and the like in a 384-well format to be suitable for HTS (FIG. 3), and NMD efficiency was measured using Wortmannin, which was a non-specific NMD inhibitor, as a control substance. Wortmannin was known to inhibit NMD by inhibiting SMG1-mediated UPF1 phosphorylation, which was a critical step in an NMD pathway (A Yamashita et al., 2001 September 1; 15(17):2215-28). As a result, as illustrated in FIG. 3, compared to an untreated group, the expression level of RLuc increased by about 10 to 40 times in the Wortmannin-treated group (in FIG. 3, w/FF luc calibration was an RLuc value corrected for a FLuc activity value). The HeLa cell line prepared above was verified to be suitable for not only reflecting the efficiency of NMD well, but also performing HTS.

Example 2. Confirmation of NMD Inhibitory Effect of Compounds 1 to 3

The NMD inhibitory effect of Compounds 1 to 3 was confirmed using the HeLa cell line prepared in Example 1. After treating the cells with Compounds 1 to 3 at 5 μM for 12 hours, respectively, total RNA and protein were purified from the cells, respectively. Then, the amounts of RNA and protein were quantified respectively through real-time PCR and dual luciferase assay methods. The results were illustrated in FIG. 4.

It was confirmed that Compound 1 increased protein translation of RLuc, whereas Compounds 2 and 3 significantly increased the amount of mRNA. From this, it could be seen that all of the three types of compounds exhibited an NMD inhibitory effect, but Compound 1 and Compounds 2 and 3 inhibited at different steps.

In conclusion, it could be seen that although the NMD steps in which each of Compounds 1 to 3 acted were slightly different, all of the compounds were substances that inhibited NMD in common.

Example 3. Analysis of NMD Inhibition Mechanism of Compounds 1 to 3

NMD was a phenomenon that occurred through several steps of protein binding, which was known to be particularly affected by binding between UPF1 and UPF2, phosphorylation of UPF1, and the like (see Korean Patent No. 1021402, etc.).

In Example 3, it was attempted to confirm on which step of NMD each compound of the present invention specifically acted.

3.1 Analysis of Effect on Phosphorylation of UPF1

Phosphorylation of UPF1 was known to be one of the most important factors in NMD. In Example 3.1, the effect of the three types of compounds of the present invention on phosphorylation of UPF1 was examined. The cells were treated with each compound at 5 μM for 12 hours, and then total proteins were purified. Then, western blotting was performed using each antibody capable of recognizing Upf1 or Upf1 phosphorylated at a specific site.

As a result, as illustrated in FIG. 5, it was confirmed that Compounds 1 and 3 did not significantly affect phosphorylation of UPF1, but Compound 2 significantly inhibited phosphorylation of UPF1.

3.2 Analysis of Effect on Binding Between UPF1 and UPF2

NMD was a phenomenon that occurred through several steps of protein binding, and among them, binding between UPF1 and UPF2 was known as the most important step. In Example 3.2, the effect of the three types of compounds of the present invention on the binding between UPF1 and UPF2 was examined.

In the cell line, DNA expressing FLAG-UPF1 was transiently overexpressed.

After treating the cell line with each compound at 5 μM for 1 hour, a cell extract was obtained. Immunoprecipitation was performed on the cell extract obtained using a FLAG antibody.

Proteins before and after immunoprecipitation were analyzed by western blotting.

As a result, as illustrated in FIG. 6, it was confirmed that Compound 1 significantly inhibited the UPF1-UPF2 binding, whereas Compounds 2 and 3 did not significantly affect the UPF1-UPF2 binding.

3.3 Analysis of Acting Step of NMD

An NMD-based search system capable of artificially reducing the amount of reporter mRNA was constructed, after artificially tethering proteins Upf1, Upf2, and Upf3X acting in each step of NMD to 3' UTR of reporter mRNA (FIG. 7). Using this method, it was attempted to verify which step of NMD the three types of compounds acted on.

As illustrated in FIG. 7, in the HeLa cell line, a plasmid expressing the reporter mRNA and MS2 binding proteins MS2-Upf1, MS2-Upf2, and MS2-Upf3 capable of binding to 3' UTR of the reporter mRNA were artificially expressed. After treating the cell line with each compound at 5 μM for 6 hours or 12 hours, a cell extract was obtained. Thereafter, the relative amount of reporter mRNA was measured through real-time PCR.

As a result, it was confirmed that Compound 1 targeted a UPF1-UPF2 step, whereas Compounds 2 and 3 did not target the UPF1-UPF2 and UPF2-UPF3 steps (FIGS. 8 and 9).

In conclusion, it was confirmed that although the NMD steps in which each of Compounds 1 to 3 acted were slightly different, all of the compounds were substances that inhibited NMD in common. Accordingly, it was confirmed that all of Compounds 1 to 3 may be effectively used for the treatment of genetic diseases caused by NMD.

Example 4. Confirmation of DMD Treatment Effect

In Example 4, in order to additionally confirm whether Compounds 1 to 3 identified as an NMD inhibitor were effective on NMD-related genetic diseases, experiments were conducted on cell lines derived from DMD patients. The DMD was a representative NMD-related genetic disease that developed by generating PTC in a dystrophin gene and quickly eliminating the PTC by NMD.

After treating two types of lymphocytes derived from different DMD patients with three types of compounds at 5 μM for 12 hours, respectively, the amount of dystrophin mRNA was quantified through real-time PCR.

As a result, it was confirmed that all of the three types of compounds increased the amount of dystrophin mRNA (DMD/GAPDH mRNA) in different DMD patient-derived cell lines (FIG. 10).

As a result of obtaining a protein from the cell line treated with Compound 1 under the same experimental conditions as described above, and examining a change in amount of dystrophin protein by Western blotting, it could be seen that the amount of dystrophin protein expressed in cells actually increased (FIG. 11).

Therefore, it was confirmed that the three types of compounds inhibited NMD and increased the amount of dystrophin.

The invention claimed is:

1. A method for treating nonsense-mediated mRNA decay (NMD)-related disease, wherein nonsense-mediated mRNA decay (NMD)-related disease is Duchenne muscular dystrophy, comprising administering to a subject in need thereof an effective amount of a compound of the following Chemical Formula 1 or a pharmaceutically acceptable salt thereof.

[Chemical Formula 1]

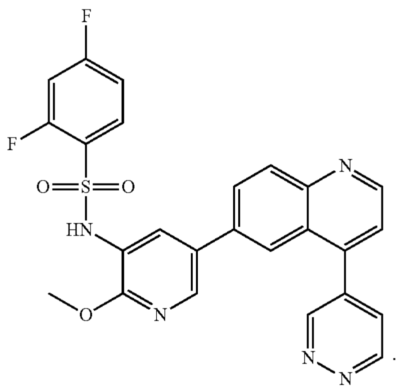

2. The method according to claim 1, wherein the compound or the pharmaceutically acceptable salt thereof inhibits nonsense-mediated mRNA decay (NMD).

3. The method according to claim 1, wherein the compound or the pharmaceutically acceptable salt thereof inhibits binding of UPF1 and UPF2.

4. The method according to claim 1, wherein the disease is genetic disease caused by NMD due to a premature termination codon (PTC) associated with a nonsense mutation or frameshift mutation.

* * * * *